(12) United States Patent
Mohseni

(10) Patent No.: US 10,996,293 B2
(45) Date of Patent: May 4, 2021

(54) SYSTEMS AND METHODS HAVING AN OPTICAL MAGNETOMETER ARRAY WITH BEAM SPLITTERS

(71) Applicant: HI LLC, Los Angeles, CA (US)

(72) Inventor: Hooman Mohseni, Wilmette, IL (US)

(73) Assignee: HI LLC, Los Angeles, CA (US)

( * ) Notice: Subject to any disclaimer, the term of this patent is extended or adjusted under 35 U.S.C. 154(b) by 0 days.

(21) Appl. No.: 16/984,752

(22) Filed: Aug. 4, 2020

(65) Prior Publication Data

US 2021/0041513 A1    Feb. 11, 2021

Related U.S. Application Data

(60) Provisional application No. 62/896,929, filed on Sep. 6, 2019, provisional application No. 62/883,406, filed on Aug. 6, 2019.

(51) Int. Cl.
*G01R 33/26*      (2006.01)

(52) U.S. Cl.
CPC ................... *G01R 33/26* (2013.01)

(58) Field of Classification Search
CPC .......................... G01R 33/26; G01N 24/006
See application file for complete search history.

(56) References Cited

U.S. PATENT DOCUMENTS

| 3,173,082 A | 3/1965 | Bell et al. |
|---|---|---|
| 3,257,608 A | 6/1966 | Bell et al. |
| 3,495,161 A | 2/1970 | Bell |
| 3,501,689 A | 3/1970 | Robbiano |
| 3,513,381 A | 5/1970 | Happer, Jr. |
| 4,193,029 A | 3/1980 | Cioccio et al. |
| 4,951,674 A | 8/1990 | Zanakis et al. |
| 5,189,368 A | 2/1993 | Chase |
| 5,192,921 A | 3/1993 | Chantry et al. |

(Continued)

FOREIGN PATENT DOCUMENTS

| CN | 104730484 | 6/2015 |
|---|---|---|
| CN | 107562188 | 1/2018 |

(Continued)

OTHER PUBLICATIONS

Hill RM, Boto E, Holmes N, et al. A tool for functional brain imaging with lifespan compliance [published correction appears in Nat Commun. Dec. 4, 2019;10(1):5628]. Nat Commun. 2019;10(1):4785. Published Nov. 5, 2019. doi:10.1038/s41467-019-12486-x.

(Continued)

*Primary Examiner* — Patrick Assouad
*Assistant Examiner* — Demetrius R Pretlow
(74) *Attorney, Agent, or Firm* — Branch Partners PLLC; Bruce E. Black

(57) ABSTRACT

An array of optically pumped magnetometers includes an array of vapor cells; and an array of beam splitters. The array of beam splitters is arranged into columns, including a first column, and rows. Each row and each column includes at least two of the beam splitters. The array of beam splitters is configured to receive light into the first column of the array and to distribute that light from the first column into each of the rows and to distribute the light from each of the rows into a plurality of individual light beams directed toward the vapor cells.

20 Claims, 5 Drawing Sheets

(56) References Cited

U.S. PATENT DOCUMENTS

| | | |
|---|---|---|
| 5,225,778 A | 7/1993 | Chaillout et al. |
| 5,254,947 A | 10/1993 | Chaillout et al. |
| 5,309,095 A | 5/1994 | Ahonen et al. |
| 5,442,289 A | 8/1995 | Dilorio et al. |
| 5,444,372 A | 8/1995 | Wikswo, Jr. et al. |
| 5,471,985 A | 12/1995 | Warden |
| 5,506,200 A | 4/1996 | Hirschkoff et al. |
| 5,526,811 A | 6/1996 | Lypchuk |
| 5,713,354 A | 2/1998 | Warden |
| 6,144,872 A | 11/2000 | Graetz |
| 6,339,328 B1 | 1/2002 | Keene et al. |
| 6,472,869 B1 | 10/2002 | Upschulte et al. |
| 6,665,553 B2 | 12/2003 | Kandori et al. |
| 6,806,784 B2 | 10/2004 | Hollberg et al. |
| 6,831,522 B2 | 12/2004 | Kitching et al. |
| 7,038,450 B2 | 5/2006 | Romalis et al. |
| 7,102,451 B2 | 9/2006 | Happer et al. |
| 7,145,333 B2 | 12/2006 | Romalis et al. |
| 7,521,928 B2 | 4/2009 | Romalis et al. |
| 7,656,154 B2 | 2/2010 | Kawabata et al. |
| 7,826,065 B1 | 11/2010 | Okandan et al. |
| 7,872,473 B2 | 1/2011 | Kitching et al. |
| 7,994,783 B2 | 8/2011 | Ledbetter et al. |
| 8,054,074 B2 | 11/2011 | Ichihara et al. |
| 8,212,556 B1 | 7/2012 | Schwindt et al. |
| 8,258,884 B2 | 9/2012 | Borwick, III et al. |
| 8,319,156 B2 | 11/2012 | Borwick, III et al. |
| 8,334,690 B2 | 12/2012 | Kitching et al. |
| 8,373,413 B2 | 2/2013 | Sugioka |
| 8,405,389 B2 | 3/2013 | Sugioka et al. |
| 8,587,304 B2 | 11/2013 | Budker et al. |
| 8,836,327 B2 | 9/2014 | French et al. |
| 8,906,470 B2 | 12/2014 | Overstolz et al. |
| 8,941,377 B2 | 1/2015 | Mizutani et al. |
| 9,084,549 B2 | 7/2015 | Desain et al. |
| 9,095,266 B1 | 8/2015 | Fu |
| 9,116,201 B2 | 8/2015 | Shah et al. |
| 9,140,590 B2 | 9/2015 | Waters et al. |
| 9,140,657 B2 | 9/2015 | Ledbetter et al. |
| 9,169,974 B2 | 10/2015 | Parsa et al. |
| 9,244,137 B2 | 1/2016 | Kobayashi et al. |
| 9,291,508 B1 | 3/2016 | Biedermann et al. |
| 9,343,447 B2 | 3/2016 | Parsa et al. |
| 9,366,735 B2 | 6/2016 | Kawabata et al. |
| 9,383,419 B2 | 7/2016 | Mizutani et al. |
| 9,395,425 B2 | 7/2016 | Diamond et al. |
| 9,417,293 B2 | 8/2016 | Schaffer et al. |
| 9,429,918 B2 | 8/2016 | Parsa et al. |
| 9,568,565 B2 | 2/2017 | Parsa et al. |
| 9,575,144 B2 | 2/2017 | Kornack et al. |
| 9,601,225 B2 | 3/2017 | Parsa et al. |
| 9,638,768 B2 | 5/2017 | Foley et al. |
| 9,639,062 B2 | 5/2017 | Dyer et al. |
| 9,677,905 B2 | 6/2017 | Waters et al. |
| 9,726,626 B2 | 8/2017 | Smith et al. |
| 9,726,733 B2 | 8/2017 | Smith et al. |
| 9,791,536 B1 | 10/2017 | Alem et al. |
| 9,829,544 B2 | 11/2017 | Bulatowicz |
| 9,846,054 B2 | 12/2017 | Waters et al. |
| 9,851,418 B2 | 12/2017 | Wolf et al. |
| 9,869,731 B1 | 1/2018 | Hovde et al. |
| 9,915,711 B2 | 3/2018 | Kornack et al. |
| 9,927,501 B2 | 3/2018 | Kim et al. |
| 9,948,314 B2 | 4/2018 | Dyer et al. |
| 9,964,609 B2 | 5/2018 | Ichihara et al. |
| 9,964,610 B2 | 5/2018 | Shah et al. |
| 9,970,999 B2 | 5/2018 | Larsen et al. |
| 9,995,800 B1 | 6/2018 | Schwindt et al. |
| 10,024,929 B2 | 7/2018 | Parsa et al. |
| 10,088,535 B1 | 10/2018 | Shah |
| 10,162,016 B2 | 12/2018 | Gabrys et al. |
| 10,194,865 B2 | 2/2019 | Le et al. |
| 10,314,508 B2 | 6/2019 | Desain et al. |
| 10,371,764 B2 | 8/2019 | Morales et al. |
| 2004/0232912 A1 | 11/2004 | Tsukamoto et al. |
| 2005/0007118 A1 | 1/2005 | Kitching et al. |
| 2005/0046851 A1 | 3/2005 | Riley, Jr. et al. |
| 2005/0206377 A1 | 9/2005 | Romalis et al. |
| 2007/0120563 A1 | 5/2007 | Kawabata et al. |
| 2007/0167723 A1 | 7/2007 | Park et al. |
| 2007/0205767 A1 | 9/2007 | Xu et al. |
| 2009/0079426 A1 | 3/2009 | Anderson |
| 2009/0101806 A1 | 4/2009 | Masuda |
| 2010/0219820 A1 | 9/2010 | Skidmore et al. |
| 2011/0062956 A1 | 3/2011 | Edelstein et al. |
| 2012/0112749 A1 | 5/2012 | Budker et al. |
| 2013/0082700 A1 | 4/2013 | Mizutani et al. |
| 2013/0082701 A1 | 4/2013 | Mizutani et al. |
| 2013/0265042 A1 | 10/2013 | Kawabata et al. |
| 2014/0121491 A1 | 5/2014 | Zhang |
| 2014/0306700 A1 | 10/2014 | Kamada et al. |
| 2014/0354275 A1 | 12/2014 | Sheng et al. |
| 2015/0022200 A1* | 1/2015 | Ichihara ............... G01R 33/26 324/304 |
| 2015/0054504 A1 | 2/2015 | Ichihara et al. |
| 2015/0378316 A1 | 12/2015 | Parsa et al. |
| 2016/0061913 A1 | 3/2016 | Kobayashi et al. |
| 2016/0116553 A1 | 4/2016 | Kim et al. |
| 2016/0223627 A1 | 8/2016 | Shah et al. |
| 2016/0291099 A1* | 10/2016 | Ueno ................. G01R 33/26 |
| 2016/0313417 A1* | 10/2016 | Kawabata ............. G02F 1/33 |
| 2017/0023653 A1 | 1/2017 | Kobayashi et al. |
| 2017/0023654 A1 | 1/2017 | Kobayashi et al. |
| 2017/0067969 A1 | 3/2017 | Butters et al. |
| 2017/0199138 A1 | 7/2017 | Parsa et al. |
| 2017/0261564 A1 | 9/2017 | Gabrys et al. |
| 2017/0331485 A1 | 11/2017 | Gobet et al. |
| 2017/0343617 A1 | 11/2017 | Manickam et al. |
| 2017/0343695 A1 | 11/2017 | Stetson et al. |
| 2017/0356969 A1* | 12/2017 | Ueno ............... G01R 33/243 |
| 2017/0360322 A1* | 12/2017 | Ueno ................. A61B 5/062 |
| 2017/0363695 A1* | 12/2017 | Ueno ............... G01R 33/032 |
| 2018/0003777 A1 | 1/2018 | Sorenson et al. |
| 2018/0038921 A1 | 2/2018 | Parsa et al. |
| 2018/0100749 A1 | 4/2018 | Waters et al. |
| 2018/0128885 A1 | 5/2018 | Parsa et al. |
| 2018/0156875 A1 | 6/2018 | Herbsommer et al. |
| 2018/0219353 A1 | 8/2018 | Shah |
| 2018/0238974 A1 | 8/2018 | Shah et al. |
| 2018/0313908 A1 | 11/2018 | Knappe et al. |
| 2018/0313913 A1 | 11/2018 | DeNatale et al. |
| 2018/0372813 A1* | 12/2018 | Bulatowicz ......... G01R 33/0041 |
| 2019/0391213 A1 | 12/2019 | Alford |
| 2020/0025844 A1 | 1/2020 | Alford et al. |
| 2020/0057115 A1 | 2/2020 | Jiménez-Martínez et al. |
| 2020/0057116 A1 | 2/2020 | Zorzos et al. |
| 2020/0064421 A1* | 2/2020 | Kobayashi ............ G01R 33/26 |
| 2020/0072916 A1 | 3/2020 | Alford et al. |
| 2020/0088811 A1 | 3/2020 | Mohseni |
| 2020/0241094 A1 | 7/2020 | Alford |

FOREIGN PATENT DOCUMENTS

| | | |
|---|---|---|
| EP | 2738627 A3 | 6/2014 |
| EP | 2380029 B1 | 10/2015 |
| EP | 3037836 B1 | 9/2017 |
| JP | 2016109665 | 6/2016 |
| JP | 2018004462 | 1/2018 |
| WO | 2005/081794 | 9/2005 |
| WO | 2014/031985 | 2/2014 |
| WO | 2017/095998 | 6/2017 |

OTHER PUBLICATIONS

Zetter, R., Iivanainen, J. & Parkkonen, L. Optical Co-registration of MRI and On-scalp MEG. Sci Rep 9, 5490 (2019). https://doi.org/10.1038/s41598-019-41763-4.

Garrido-Jurado, Sergio, Rafael Muñoz-Salinas, Francisco José Madrid-Cuevas and Manuel J. Marín-Jiménez. "Automatic generation and detection of highly reliable fiducial markers under occlusion." Pattern Recognit. 47 (2014): 2280-2292.

Hill RM, Boto E, Rea M, et al. Multi-channel whole-head OPM-MEG: Helmet design and a comparison with a conventional system

(56) References Cited

OTHER PUBLICATIONS

[published online ahead of print, May 29, 2020]. Neuroimage. 2020;219:116995. doi:10.1016/j.neuroimage.2020.116995.

V. Kazemi and J. Sullivan, "One millisecond face alignment with an ensemble of regression trees," 2014 IEEE Conference on Computer Vision and Pattern Recognition, Columbus, OH, 2014, pp. 1867-1874, doi: 10.1109/CVPR.2014.241.

Holmes, N., Tierney, T.M., Leggett, J. et al. Balanced, bi-planar magnetic field and field gradient coils for field compensation in wearable magnetoencephalography. Sci Rep 9, 14196 (2019).

N. Holmes, J. Leggett, E. Boto, G. Roberts, R.M. Hill, T.M. Tierney, V. Shah, G.R. Barnes, M.J. Brookes, R. Bowtell a bi-planar coil system for nulling background magnetic fields in scalp mounted magnetoencephalography Neuroimage, 181 (2018), pp. 760-774.

J. M. Leger et. al., In-flight performance of the Absolute Scalar Magnetometer vector mode on board the Swarm satellites, Earth, Planets, and Space (2015) 67:57.

Alexandrov, E. B., Balabas, M. V., Kulyasov, V. N., Ivanov, A. E., Pazgalev, A. S., Rasson, J. L., . . . (2004). Three-component variometer based on a scalar potassium sensor. Measurement Science and Technology, 15(5), 918-922.

Gravrand, O., Khokhlov, A., & JL, L. M. (2001). On the calibration of a vectorial 4He pumped magnetometer. Earth, planets and space, 53 (10), 949-958.

Borna, Amir & Carter, Tony & Colombo, Anthony & Jau, Y-Y & McKay, Jim & Weisend, Michael & Taulu, Samu & Stephen, Julia & Schwindt, Peter. (2018). Non-Invasive Functional-Brain-Imaging with a Novel Magnetoencephalography System. 9 Pages.

Vrba J, Robinson SE. Signal processing in magnetoencephalography. Methods. 2001;25(2):249-271. doi:10.1006/meth.2001.1238.

Uusitalo M and Ilmoniemi R., 1997, Signal-space projection method for separating MEG or EEG into components. Med. Biol. Comput. (35) 135-140.

Taulu S and Kajola M., 2005, Presentation of electromagnetic multichannel data: the signal space separation method. J. Appl. Phys. (97) 124905 (2005).

Taulu S, Simola J and Kajola M., 2005, Applications of the signal space separation method. IEEE Trans. Signal Process. (53) 3359-3372 (2005).

Taulu S, Simola J., 2006, Spatiotemporal signal space separation method for rejecting nearby interference in MEG measurements. Phys. Med. Biol. (51) 1759-1768 (2006).

Johnson, et al., Magnetoencephalography with a two-color pump-probe, fiber-coupled atomic magnetometer, Applied Physics Letters 97, 243703 2010.

Zhang, et al., Magnetoencephalography using a compact multichannel atomic magnetometer with pump-probe configuration, AIP Advances 8, 125028 (2018).

Xia, H. & Ben-Amar Baranga, Andrei & Hoffman, D. & Romalis, Michael. (2006). Magnetoencephalography with an atomic magnetometer. Applied Physics Letters—Appl Phys Lett. 89. 10.1063/1.2392722.

Ilmoniemi, R. (2009). The triangle phantom in magnetoencephalography. In 24th Annual Meeting of Japan Biomagnetism and Bioelecctromagnetics Society, Kanazawa, Japan, 28.29.5.2009 (pp. 6263).

Oyama D. Dry phantom for magnetoencephalography—Configuration, calibration, and contribution. J Neurosci Methods. 2015;251:24-36. doi: 0.1016/j.jneumeth.2015.05.004.

Chutani, R., Maurice, V., Passilly, N. et al. Laser light routing in an elongated micromachined vapor cell with diffraction gratings for atomic clock applications. Sci Rep 5, 14001 (2015). https://doi.org/10.1038/srep14001.

Eklund, E. Jesper, Andrei M. Shkel, Svenja Knappe, Elizabeth A. Donley and John Kitching. "Glass-blown spherical microcells for chip-scale atomic devices." (2008).

Jiménez-Martínez R, Kennedy DJ, Rosenbluh M, et al. Optical hyperpolarization and NMR detection of 129Xe on a microfluidic chip. Nat Commun. 2014;5:3908. Published May 20, 2014. doi:10.1038/ncomms4908.

Boto, Elena, Sofie S. Meyer, Vishal Shah, Orang Alem, Svenja Knappe, Peter Kruger, T. Mark Fromhold, et al. "A New Generation of Magnetoencephalography: Room Temperature Measurements Using Optically-Pumped Magnetometers." NeuroImage 149 (Apr. 1, 2017): 404-14.

Bruno, A. C., and P. Costa Ribeiro. "Spatial Fourier Calibration Method for Multichannel SQUID Magnetometers." Review of Scientific Instruments 62, No. 4 (Apr. 1, 1991): 1005-9.

Chella, Federico, Filippo Zappasodi, Laura Marzetti, Stefania Della Penna, and Vittorio Pizzella. "Calibration of a Multichannel MEG System Based on the Signal Space Separation Method." Physics in Medicine and Biology 57 (Jul. 13, 2012): 4855-70.

Pasquarelli, A, M De Melis, Laura Marzetti, Hans-Peter Müller, and S N Erné. "Calibration of a Vector-MEG Helmet System." Neurology & Clinical Neurophysiology: NCN 2004 (Feb. 1, 2004): 94.

Pfeiffer, Christoph, Lau M. Andersen, Daniel Lundqvist, Matti Hämäläinen, Justin F. Schneiderman, and Robert Oostenveld. "Localizing On-Scalp MEG Sensors Using an Array of Magnetic Dipole Coils." PLOS One 13, No. 5 (May 10, 2018): e0191111.

Vivaldi, Valentina, Sara Sommariva, and Alberto Sorrentino. "A Simplex Method for the Calibration of a MEG Device." Communications in Applied and Industrial Mathematics 10 (Jan. 1, 2019): 35-46.

Nagel, S., & Spüler, M. (2019). Asynchronous non-invasive high-speed BCI speller with robust non-control state detection. Scientific Reports, 9(1), 8269.

Thielen, J., van den Broek, P., Farquhar, J., & Desain, P. (2015). Broad-Band Visually Evoked Potentials: Re(con) volution in Brain-Computer Interfacing. PloS One, 10(7), e0133797. https://doi.org/10.1371/journal.pone.0133797.

J. Kitching, "Chip-scale atomic devices," Appl. Phys. Rev. 5(3), 031302 (2018), 39 pages.

Allred, J. C., Lyman, R. N., Kornack, T. W., & Romalis, M. V. (2002). High-sensitivity atomic magnetometer unaffected by spin-exchange relaxation. Physical review letters, 89(13), 130801.

Balabas et al. Polarized alkali vapor with minute-long transverse spin-relaxation time, Phys. Rev. Lett. 105, 070801—Published Aug. 12, 2010.

Barbieri, F., Trauchessec, V., Caruso, L., Trejo-Rosillo, J., Telenczuk, B., Paul, E., . . . & Ouanounou, G. (2016). Local recording of biological magnetic fields using Giant Magneto Resistance-based micro-probes. Scientific reports, 6, 39330.

Dmitry Budker and Michael Romalis, "Optical Magnetometry," Nature Physics, 2008, https://arxiv.org/abs/physics/0611246v1.

Anthony P. Colombo, Tony R. Carter, Amir Borna, Yuan-Yu Jau, Cort N. Johnson, Amber L. Dagel, and Peter D. D. Schwindt, "Four-channel optically pumped atomic magnetometer for magnetoencephalography," Opt. Express 24, 15403-15416 (2016).

Dang, H.B. & Maloof, A.C. & Romalis, Michael. (2009). Ultra-high sensitivity magnetic field and magnetization measurements with an atomic magnetometer. Applied Physics Letters. 97. 10.1063/1.3491215.

Donley, E.A. & Hodby, E & Hollberg, L & Kitching, J. (2007). Demonstration of high-performance compact magnetic shields for chip-scale atomic devices. The Review of scientific instruments. 78. 083102.

Hämäläinen, Matti & Hari, Riitta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics. vol. 65, Issue 2. 413-497.

Hunter, D. and Piccolomo, S. and Pritchard, J. D. and Brockie, N. L. and Dyer, T. E. and Riis, E. (2018) Free-induction-decay magnetometer based on a microfabricated Cs vapor cell. Physical Review Applied (10).ISSN 2331-7019.

Jiménez-Martínez, R., Griffith, W. C., Wang, Y. J., Knappe, S., Kitching, J., Smith, K., & Prouty, M. D. (2010). Sensitivity comparison of Mx and frequency-modulated bell-bloom Cs magnetometers in a microfabricated cell. IEEE Transactions on Instrumentation and Measurement, 59(2), 372-378.

Kiwoong Kim, Samo Begus, Hui Xia, Seung-Kyun Lee, Vojko Jazbinsek, Zvonko Trontelj, Michael V. Romalis, Multi-channel atomic magnetometer for magnetoencephalography: A configura-

(56) References Cited

OTHER PUBLICATIONS tion study. NeuroImage 89 (2014) 143-151 http://physics.princeton.edu/romalis/papers/Kim_2014.pdf.

Knappe, Svenja & Sander, Tilmann & Trahms, Lutz. (2012). Optically-Pumped Magnetometers for MEG. Magnetoencephalography: From Signals to Dynamic Cortical Networks. 993-999. 10.1007/978-3-642-33045-2_49.

Kominis, I.K., Kornack, T.W., Allred, J.C. and Romalis, M.V., 2003. A subfemtotesla multichannel atomic magnetometer. Nature, 422(6932), p. 596.

Korth, H., K. Strohbehn, F. Tejada, A. G. Andreou, J. Kitching, S. Knappe, S. J. Lehtonen, S. M. London, and M. Kafel (2016), Miniature atomic scalar magnetometer for space based on the rubidium isotope 87Rb, J. Geophys. Res. Space Physics, 121, 7870-7880, doi:10.1002/2016JA022389.

Lenz, J. and Edelstein, S., 2006. Magnetic sensors and their applications. IEEE Sensors journal, 6(3), pp. 631-649.

Li, S & Vachaspati, Pranjal & Sheng, Dehong & Dural, Nezih & Romalis, Michael. (2011). Optical rotation in excess of 100 rad generated by Rb vapor in a multipass cell. Phys. Rev. A. 84. 10.1103/PhysRevA.84.061403.

Maze, J. R., Stanwix, P. L., Hodges, J. S., Hong, S., Taylor, J. M., Cappellaro, P., . . . & Yacoby, A. (2008). Nanoscale magnetic sensing with an individual electronic spin in diamond. Nature, 455(7213), 644.

Sander TH, Preusser J, Mhaskar R, Kitching J, Trahms L, Knappe S. Magnetoencephalography with a chip-scale atomic magnetometer. Biomed Opt Express. 2012;3(5):981-90.

J. Seltzer, S & Romalis, Michael. (2010). High-temperature alkali vapor cells with antirelaxation surface coatings. Journal of Applied Physics. 106. 114905-114905. 10.1063/1.3236649.

Seltzer, S. J., and Romalis, M.V., "Unshielded three-axis vector operation of a spin-exchange-relaxation-free atomic magnetometer." Applied physics letters 85.20 (2004):4804-4806.

Sheng, Dong & R. Perry, Abigail & Krzyzewski, Sean & Geller, Shawn & Kitching, John & Knappe, Svenja. (2017). A microfabricated optically-pumped magnetic gradiometer. Applied Physics Letters. 110. 10.1063/1.4974349.

Sheng, Dehong & Li, S & Dural, Nezih & Romalis, Michael. (2013). Subfemtotesla Scalar Atomic Magnetometry Using Multipass Cells. Physical review letters. 110. 160802. 10.1103/PhysRevLett.110.160802.

Volkmar Schultze et al. An Optically Pumped Magnetometer Working in the Light-Shift Dispersed Mz Mode, Sensors 2017, 17, 561; doi:10.3390/s17030561.

Fang, J. and Qin, J., 2012. In situ triaxial magnetic field compensation for the spin-exchange-relaxation-free atomic magnetometer. Review of Scientific Instruments, 83(10), p. 103104.

Joon Lee, Hyun & Shim, Jeong & Moon, Han Seb & Kim, Kiwoong. (2014). Flat-response spin-exchange relaxation free atomic magnetometer under negative feedback. Optics Express. 22. 10.1364/OE.22.019887.

Griffith, Clark & Jimenez-Martinez, Ricardo & Shah, Vishal & Knappe, Svenja & Kitching, John. (2009). Miniature atomic magnetometer integrated with flux concentrators. Applied Physics Letters—Appl Phys Lett. 94. 10.1063/1.3056152.

Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.2885711.

Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-018-20352-x.

Kim, Young Jin & Savukov, I. (2016). Ultra-sensitive Magnetic Microscopy with an Optically Pumped Magnetometer. Scientific Reports. 6. 24773. 10.1038/srep24773.

Navau, Carles & Prat-Camps, Jordi & Sanchez, Alvaro. (2012). Magnetic Energy Harvesting and Concentration at a Distance by Transformation Optics. Physical review letters. 109. 263903. 10.1103/PhysRevLett.109.263903.

Orang Alem, Rahul Mhaskar, Ricardo Jiménez-Martínez, Dong Sheng, John LeBlanc, Lutz Trahms, Tilmann Sander, John Kitching, and Svenja Knappe, "Magnetic field imaging with microfabricated optically-pumped magnetometers," Opt. Express 25, 7849-7858 (2017).

Slocum et al., Self-Calibrating Vector Magnetometer for Space, https://esto.nasa.gov/conferences/estc-2002/Papers/B3P4(Slocum).pdf.

Dupont-Roc, J & Haroche, S & Cohen-Tannoudji, C. (1969). Detection of very weak magnetic fields (10-9gauss) by 87Rb zero-field level crossing resonances. Physics Letters A—Phys Lett A. 28. 638-639. 10.1016/0375-9601(69)90480-0.

J. A. Neuman, P. Wang, and A. Gallagher, Robust high-temperature sapphire cell for metal vapors, Review of Scientific Instruments, vol. 66, Issue 4, Apr. 1995, pp. 3021-3023.

Borna, Amir, et al. "A 20-channel magnetoencephalography system based on optically pumped magnetometers." Physics in Medicine & Biology 62.23 (2017): 8909.

R. E. Slocum & L. J. Ryan, Design and operation of the minature vector laser magnetometer, Nasa Earth Science Technology Conference 2003.

Schoenmaker, Jeroen & R Pirota, K & Teixeira, Julio. (2013). Magnetic flux amplification by Lenz lenses. The Review of scientific instruments. 84. 085120. 10.1063/1.4819234.

Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic modulator detection in the optically pumped magnetometer. Applied Optics. 56. 5927. 10.1364/AO.56.005927.

Masuda, Y & Ino, T & Skoy, Vadim & Jones, G.L. (2005). 3He polarization via optical pumping in a birefringent cell. Applied Physics Letters. 87. 10.1063/1.2008370.

A.B. Baranga et al., An atomic magnetometer for brain activity imaging, Real Time Conference 2005. 14th IEEE-NPSS. pp. 417-418.

Larry J. Ryan, Robert E. Slocum, and Robert B. Steves, Miniature Vector Laser Magnetometer Measurements of Earth's Field, May 10, 2004, 4 pgs.

Lorenz, V. O., Dai, X., Green, H., Asnicar, T. R., & Cundiff, S. T. (2008). High-density, high-temperature alkali vapor cell. Review of Scientific Instruments, 79(12), 4 pages.

F. Jackson Kimball, D & Dudley, J & Li, Y & Thulasi, Swecha & Pustelny, Szymon & Budker, Dmitry & Zolotorev, Max. (2016). Magnetic shielding and exotic spin-dependent interactions. Physical Review D. 94. 10.1103/PhysRevD.94.082005.

Huang, Haichao, et al. "Single-beam three-axis atomic magnetometer." Applied Physics Letters 109.6 (2016): 062404. (Year: 2016).

Scott Jeffrey Seltzer: "Developments in alkali-metal atomic magnetometry", Nov. 1, 2008 (Nov. 1, 2008), XP055616618, ISBN: 978-0-549-93355-7 Retrieved from the Internet: URL:http://physics.princeton.edu/atomic/romalis/papers/Seltzer%20Thesis.pdf [retrieved on Aug. 29, 2019] pp. 148-159.

Haifeng Dong et al: "Atomic-Signal-Based Zero-Field Finding Technique for Unshielded Atomic Vector Magnetometer", IEEE Sensors Journal, IEEE Service Center, New York, NY, US, vol. 13, No. 1, Jan. 1, 2013 (Jan. 1, 2013), pp. 186-189.

Boto, E, Holmes, N, Leggett, J, Roberts, G, Shah, V, Meyer, SS, Muñoz, LD, Mullinger, KJ, Tierney, TM, Bestmann, S, Barnes, GR, Bowtell, R & Brookes, MJ 2018, 'Moving magnetoencephalography towards real world applications with a wearable system', Nature, vol. 555, pp. 657-661.

Ijsselsteijn, R & Kielpinski, Mark & Woetzel, S & Scholtes, Theo & Kessler, Ernst & Stolz, Ronny & Schultze, V & Meyer, H-G. (2012). A full optically operated magnetometer array: An experimental study. The Review of scientific instruments. 83. 113106. 10.1063/1.4766961.

Tierney, T. M., Holmes, N., Meyer, S. S., Boto, E., Roberts, G., Leggett, J., . . . Barnes, G. R. (2018). Cognitive neuroscience using

(56) References Cited

OTHER PUBLICATIONS wearable magnetometer arrays: Non-invasive assessment of language function. NeuroImage, 181, 513-520.

Manon Kok, Jeroen D. Hol and Thomas B. Schon (2017), "Using Inertial Sensors for Position and Orientation Estimation", Foundations and Trends in Signal Processing: vol. 11: No. 1-2, pp. 1-153. http://dx.doi.org/10.1561/2000000094.

* cited by examiner

SYSTEMS AND METHODS HAVING AN OPTICAL MAGNETOMETER ARRAY WITH BEAM SPLITTERS

CROSS-REFERENCE TO RELATED APPLICATIONS

This application claims the benefit of U.S. Provisional Patent Application Ser. Nos. 62/883,406, filed Aug. 6, 2019, and 62/896,929, filed Sep. 6, 2019, both of which are incorporated herein by reference in their entireties.

FIELD

The present disclosure is directed to the area of magnetic field measurement systems including systems for magnetoencephalography (MEG). The present disclosure is also directed to methods and systems having an array of optically pumped magnetometers (OPM) and an array of beam splitters for applications such as high spatial resolution MEG.

BACKGROUND

In the nervous system, neurons propagate signals via action potentials. These are brief electric currents which flow down the length of a neuron causing chemical transmitters to be released at a synapse. The time-varying electrical currents within an ensemble of neurons generates a magnetic field. Magnetoencephalography (MEG), the measurement of magnetic fields generated by the brain, is one method for observing these neural signals.

Existing technology for measuring MEG typically utilizes superconducting quantum interference devices (SQUIDs) or collections of discrete optically pumped magnetometers (OPMs). SQUIDs require cryogenic cooling, which is bulky, expensive, requires a lot of maintenance. These requirements preclude their application to mobile or wearable devices.

An alternative to an array of SQUIDs is an array of OPMs. For MEG and other applications, the array of OPMS may have a large number of OPM sensors that are tightly packed. Such dense arrays can produce a high resolution spatial mapping of the magnetic field, and at a very high sensitivity level. Such OPMs sensors can be used for a wide range of applications, including sensing magnetic field generated by neural activities, similar to MEG systems.

BRIEF SUMMARY

One embodiment is an array of optically pumped magnetometers that includes an array of vapor cells; and an array of beam splitters. The array of beam splitters is arranged into columns, including a first column, and rows. Each row and each column includes at least two of the beam splitters. The array of beam splitters is configured to receive light into the first column of the array and to distribute that light from the first column into each of the rows and to distribute the light from each of the rows into a plurality of individual light beams directed toward the vapor cells.

In at least some embodiments, the array of vapor cells is an N×M array and the array of beam splitters is an (N+1)×M array, wherein N and M are integers greater than one. In at least some embodiments, the array of beam splitters is configured to generate N×M beams of light. In at least some embodiments, the N×M beams of light have intensities that differ by no more than 5% from each other.

In at least some embodiments, the first column has M of the beam splitters and the m-th one of the beam splitters in the first column has a reflectivity of 1/(M−m+1), wherein M is an integer greater than one and m is an integer ranging from 1 to M. In at least some embodiments, at least one row has a one of the beam splitters from the first column followed by N of the beam splitters after, wherein the n-th one of the N beam splitters has a reflectivity of 1/(N−n+1), wherein N is an integer greater than one and n is an integer ranging from 1 to N.

In at least some embodiments, the array of optically pumped magnetometers further includes a quarter waveplate disposed between the array of beam splitters and the array of vapor cells. In at least some embodiments, the array of optically pumped magnetometers further includes a light source configured and arranged to direct light into the first column of the array of beam splitters. In at least some embodiments, the array of optically pumped magnetometers further includes a reference detector configured to receive light that has passed through the beam splitters of the first column.

In at least some embodiments, the beam splitters are polarizing beam splitters. In at least some embodiments, the array of optically pumped magnetometers further includes waveplates disposed between adjacent ones of the polarizing beam splitters to rotate a polarization of a light beam exiting one of the polarizing beam splitters prior to entering another one of the polarizing beam splitters.

In at least some embodiments, the beam splitters are bonded together into a single block using optical adhesive.

Another embodiment is a magnetic field measurement system that includes an array of vapor cells; an array of light detectors configured to receive light passing through the vapor cells; and an array of beam splitters. The array of beam splitters is arranged into columns, including a first column, and rows. Each row and each column includes at least two of the beam splitters. The array of beam splitters is configured to receive light into the first column of the array and to distribute that light from the first column into each of the plurality of rows and to distribute the light from each of the rows into a plurality of individual light beams directed toward the vapor cells.

In at least some embodiments, the magnetic field measurement system further includes at least one magnetic field generator disposed around at least one of the vapor cells to generate a magnetic field in the vapor cell. In at least some embodiments, the magnetic field measurement system further includes a light source configured and arranged to direct light into the first column of the array of beam splitters. In at least some embodiments, the magnetic field measurement system further includes a computing device coupled to the array of light detectors and the light source.

In at least some embodiments, the magnetic field measurement system further includes a wearable article within which the array of vapor cells, array of light detectors and array of beam splitters are disposed. In at least some embodiments, the magnetic field measurement system further includes a light source disposed in the wearable article and configured and arranged to direct light into the first column of the array of beam splitters.

In at least some embodiments, the first column has M of the beam splitters and the m-th one of the beam splitters in the first column has a reflectivity of 1/(M−m+1), wherein M is an integer greater than one and m is an integer ranging from 1 to M. In at least some embodiments, at least one row has a one of the beam splitters from the first column followed by N of the beam splitters after, wherein the n-th one of the N beam splitters has a reflectivity of 1/(N−n+1), wherein N is an integer greater than one and n is an integer ranging from 1 to N.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1A:
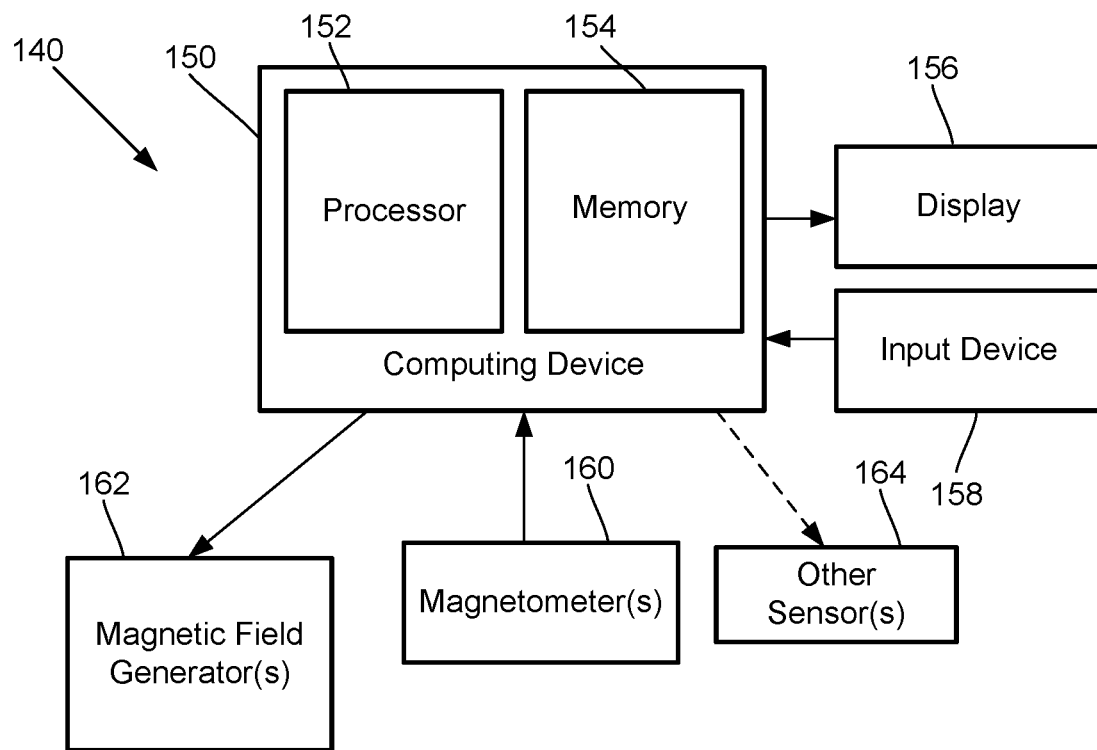
FIG. 1A is a schematic block diagram of one embodiment of a magnetic field measurement system, according to the invention.

The present disclosure is directed to the area of magnetic field measurement systems including systems for magnetoencephalography (MEG). The present disclosure is also directed to methods and systems having an array of optically pumped magnetometers (OPM) and an array of beam splitters for applications such as high spatial resolution MEG.

Herein the terms "ambient background magnetic field" and "background magnetic field" are interchangeable and used to identify the magnetic field or fields associated with sources other than the magnetic field measurement system and the magnetic field sources of interest, such as biological source(s) (for example, neural signals from a user's brain) or non-biological source(s) of interest. The terms can include, for example, the Earth's magnetic field, as well as magnetic fields from magnets, electromagnets, electrical devices, and other signal or field generators in the environment, except for the magnetic field generator(s) that are part of the magnetic field measurement system.

The terms "gas cell", "vapor cell", and "vapor gas cell" are used interchangeably herein. Below, a gas cell containing alkali metal vapor is described, but it will be recognized that other gas cells can contain different gases or vapors for operation.

The methods and systems are described herein using optically pumped magnetometers (OPMs). While there are many types of OPMs, in general magnetometers operate in two modalities: vector mode and scalar mode. In vector mode, the OPM can measure one, two, or all three vector components of the magnetic field; while in scalar mode the OPM can measure the total magnitude of the magnetic field.

Vector mode magnetometers measure a specific component of the magnetic field, such as the radial and tangential components of magnetic fields with respect the scalp of the human head. Vector mode OPMs often operate at zero-field and may utilize a spin exchange relaxation free (SERF) mode to reach femto-Tesla sensitivities. A SERF mode OPM is one example of a vector mode OPM, but other vector mode OPMs can be used at higher magnetic fields. These SERF mode magnetometers can have high sensitivity but may not function in the presence of magnetic fields higher than the linewidth of the magnetic resonance of the atoms of about 10 nT, which is much smaller than the magnetic field strength generated by the Earth.

Magnetometers operating in the scalar mode can measure the total magnitude of the magnetic field. (Magnetometers in the vector mode can also be used for magnitude measurements.) Scalar mode OPMs often have lower sensitivity than SERF mode OPMs and are capable of operating in higher magnetic field environments.

The magnetic field measurement systems, such as a biological signal detection system, described herein can be used to measure or observe electromagnetic signals generated by one or more magnetic field sources (for example, neural signals or other biological sources) of interest. The system can measure biologically generated magnetic fields and, at least in some embodiments, can measure biologically generated magnetic fields in an unshielded or partially shielded environment. Aspects of a magnetic field measurement system will be exemplified below using magnetic signals from the brain of a user; however, biological signals from other areas of the body, as well as non-biological signals, can be measured using the system. In at least some embodiments, the system can be a wearable MEG system that can be portable and used outside a magnetically shielded room.

A magnetic field measurement system, such as a biological signal detection system, can utilize one or more magnetic field sensors. Magnetometers will be used herein as an example of magnetic field sensors, but other magnetic field sensors may also be used in addition to, or as an alternative to, the magnetometers. FIG. 1A is a block diagram of components of one embodiment of a magnetic field measurement system 140 (such as a biological signal detection system.) The system 140 can include a computing device 150 or any other similar device that includes a processor 152, a memory 154, a display 156, an input device 158, one or more magnetometers 160 (for example, an array of magnetometers) which can be OPMs, one or more magnetic field generators 162, and, optionally, one or more other sensors 164 (e.g., non-magnetic field sensors). The system 140 and its use and operation will be described herein with respect to the measurement of neural signals arising from one or more magnetic field sources of interest in the brain of a user as an example. It will be understood, however, that the system can be adapted and used to measure signals from other magnetic field sources of interest including, but not limited to, other neural signals, other biological signals, as well as non-biological signals.

The computing device 150 can be a computer, tablet, mobile device, field programmable gate array (FPGA), microcontroller, or any other suitable device for processing information or instructions. The computing device 150 can be local to the user or can include components that are non-local to the user including one or both of the processor 152 or memory 154 (or portions thereof). For example, in at least some embodiments, the user may operate a terminal that is connected to a non-local computing device. In other embodiments, the memory 154 can be non-local to the user.

The computing device 150 can utilize any suitable processor 152 including one or more hardware processors that may be local to the user or non-local to the user or other components of the computing device. The processor 152 is configured to execute instructions stored in the memory 154.

Any suitable memory 154 can be used for the computing device 150. The memory 154 illustrates a type of computer-readable media, namely computer-readable storage media. Computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 156 can be any suitable display device, such as a monitor, screen, or the like, and can include a printer. In some embodiments, the display is optional. In some embodiments, the display 156 may be integrated into a single unit with the computing device 150, such as a tablet, smart phone, or smart watch. In at least some embodiments, the display is not local to the user. The input device 158 can be, for example, a keyboard, mouse, touch screen, track ball, joystick, voice recognition system, or any combination thereof, or the like. In at least some embodiments, the input device is not local to the user.

The magnetic field generator(s) 162 can be, for example, Helmholtz coils, solenoid coils, planar coils, saddle coils, electromagnets, permanent magnets, or any other suitable arrangement for generating a magnetic field. As an example, the magnetic field generator 162 can include three orthogonal sets of coils to generate magnetic fields along three orthogonal axes. Other coil arrangement can also be used. The optional sensor(s) 164 can include, but are not limited to, one or more position sensors, orientation sensors, accelerometers, image recorders, or the like or any combination thereof.

The one or more magnetometers 160 can be any suitable magnetometer including, but not limited to, any suitable optically pumped magnetometer. Arrays of magnetometers are described in more detail herein. In at least some embodiments, at least one of the one or more magnetometers (or all of the magnetometers) of the system is arranged for operation in the SERF mode.

Figure 1B:
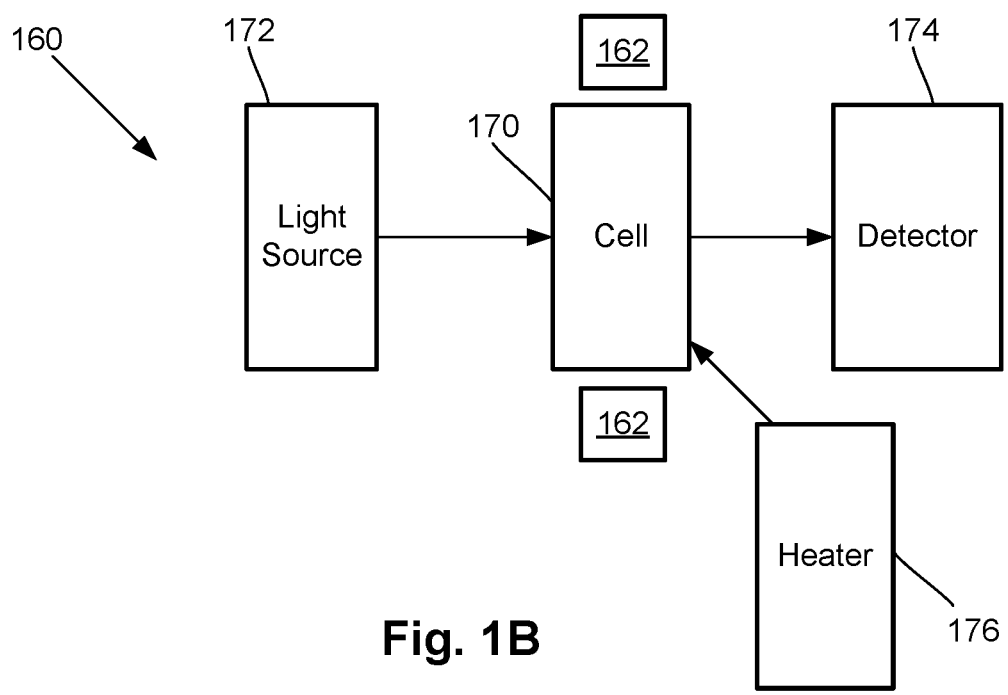
FIG. 1B is a schematic block diagram of one embodiment of a magnetometer, according to the invention.

FIG. 1B is a schematic block diagram of one embodiment of a magnetometer 160 which includes a vapor cell 170 (also referred to as a "cell") such as an alkali metal vapor cell; a heating device 176 to heat the cell 170; a light source 172; and a detector 174. In addition, coils of a magnetic field generator 162 can be positioned around the vapor cell 170. The vapor cell 170 can include, for example, an alkali metal vapor (for example, rubidium in natural abundance, isotopically enriched rubidium, potassium, or cesium, or any other suitable alkali metal such as lithium, sodium, or francium) and, optionally, one, or both, of a quenching gas (for example, nitrogen) and a buffer gas (for example, nitrogen, helium, neon, or argon). In some embodiments, the vapor cell may include the alkali metal atoms in a prevaporized form prior to heating to generate the vapor.

The light source 172 can include, for example, a laser to, respectively, optically pump the alkali metal atoms and probe the vapor cell. The light source 172 may also include optics (such as lenses, waveplates, collimators, polarizers, and objects with reflective surfaces) for beam shaping and polarization control and for directing the light from the light source to the cell and detector. Examples of suitable light sources include, but are not limited to, a diode laser (such as a vertical-cavity surface-emitting laser (VCSEL), distributed Bragg reflector laser (DBR), or distributed feedback laser (DFB)), light-emitting diode (LED), lamp, or any other suitable light source. In some embodiments, the light source 172 may include two light sources: a pump light source and a probe light source.

The detector 174 can include, for example, an optical detector to measure the optical properties of the transmitted probe light field amplitude, phase, or polarization, as quantified through optical absorption and dispersion curves, spectrum, or polarization or the like or any combination thereof. Examples of suitable detectors include, but are not limited to, a photodiode, charge coupled device (CCD) array, CMOS array, camera, photodiode array, single photon avalanche diode (SPAD) array, avalanche photodiode (APD) array, or any other suitable optical sensor array that can measure the change in transmitted light at the optical wavelengths of interest.

Figure 2:
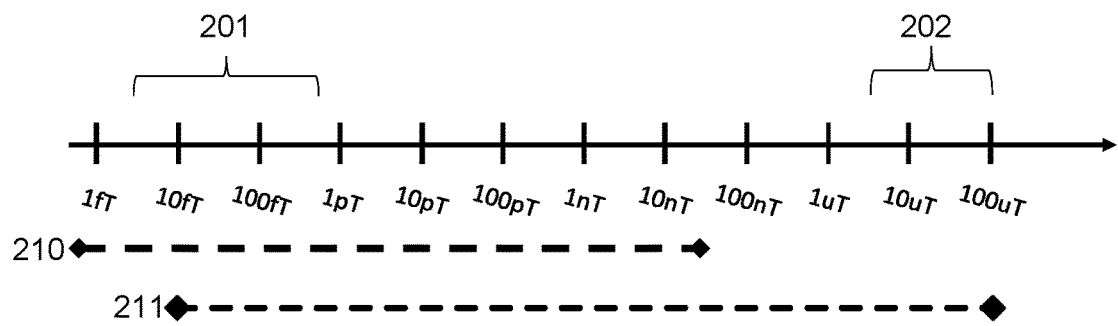
FIG. 2 shows a magnetic spectrum with lines indicating dynamic ranges of magnetometers operating in different modes.

FIG. 2 shows the magnetic spectrum from 1 fT to 100 µT in magnetic field strength on a logarithmic scale. The magnitude of magnetic fields generated by the human brain are indicated by range 201 and the magnitude of the background ambient magnetic field, including the Earth's magnetic field, by range 202. The strength of the Earth's magnetic field covers a range as it depends on the position on the Earth as well as the materials of the surrounding environment where the magnetic field is measured. Range 210 indicates the approximate measurement range of a magnetometer (e.g., an OPM) operating in the SERF mode (e.g., a SERF magnetometer) and range 211 indicates the approximate measurement range of a magnetometer operating in a scalar mode (e.g., a scalar magnetometer.) Typically, a SERF magnetometer is more sensitive than a scalar magnetometer but many conventional SERF magnetometers typically only operate up to about 0 to 200 nT while the scalar magnetometer starts in the 10 to 100 fT range but extends above 10 to 100 µT.

The systems and methods described herein will utilize OPMs, but it will be understood that other magnetometers can be used in addition to, or instead of, OPMs. In at least some embodiments, the OPMs utilize laser light for pumping and probing the vapor cell of the OPM. When an array of OPMs is used, the laser light is delivered to each OPM vapor cell in the array. Individual lasers could be used for the individual OPMs, but such an arrangement is inefficient and may result in substantial noise as the noise in each laser can vary independently of the others. One conventional method for providing laser light to multiple vapor cells utilizes fiber splitters which divide the optical beam of one or more lasers for delivery into multiple optical fibers. The optical fibers deliver the laser light to the individual vapor cells of the OPMs. A challenge with this approach is the large number of fibers involved, as well as the noise generated due to polarization shifting arising from mechanical deformation of the fibers (even from polarization maintaining fibers).

Another conventional approach divides the beam from one laser into four different sensing regions within a sensor head using a diffractive optical element. However, this arrangement has a relatively large distance between the diffraction element and a lens to collimate the laser light because the deflection angle of the diffraction element cannot be very large. In addition, the numerical aperture (NA) of the lens also limits this distance. In addition, this approach may not be scalable for systems with significantly more than four channels.

In contrast to these conventional arrangements, in at least some embodiments, a system or method includes splitting the beam(s) of one or more surface emitting lasers using an array of beam splitters. In at least some embodiments, the array of beam splitters forms a two-dimensional grid.

Figure 3A:
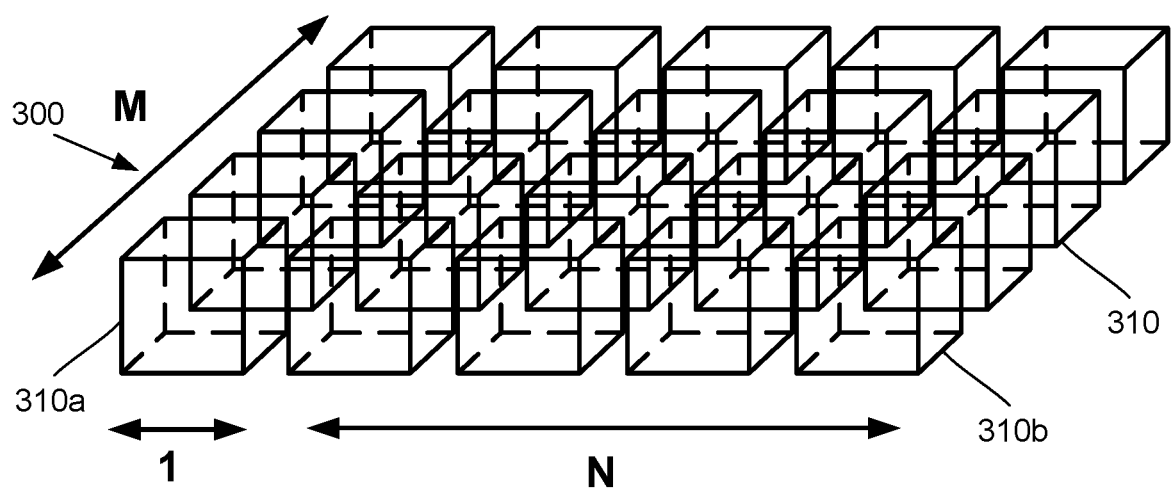
FIG. 3A is a perspective view of one embodiment of an array of beam splitters for use with an array of magnetometers, according to the invention.
Figure 3B:
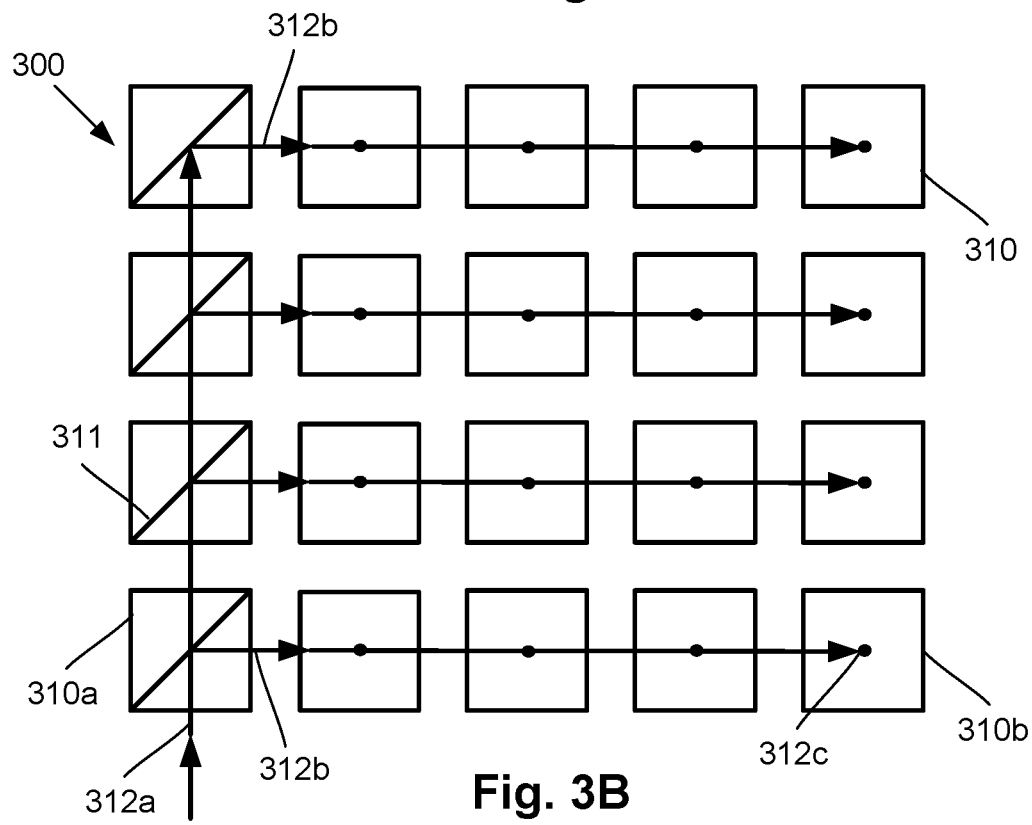
FIG. 3B is a top view of the array of beam splitters of FIG. 3A, according to the invention.
Figure 3C:
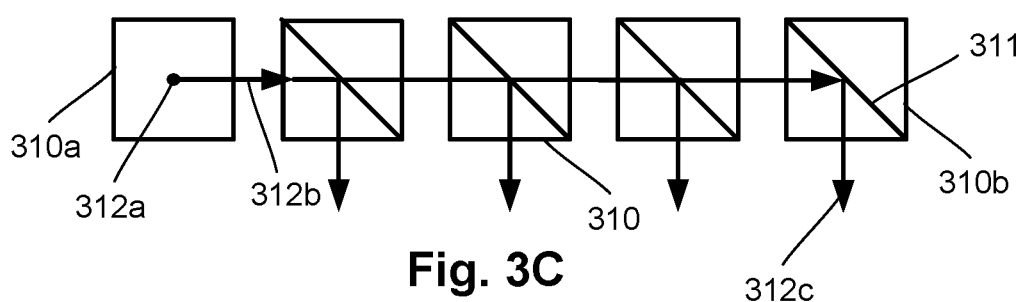
FIG. 3C is a front view of one row of the array of beam splitters of FIG. 3A, according to the invention.

FIGS. 3A-3C illustrate one embodiment of an array 300 of beam splitters 310 (which may be in the form of cubes or any other suitable shape) for use with an N×M array of OPMs or other magnetometers. FIG. 3B is a top view of the array 300 and FIG. 3C is a front view of one row of the beam splitters 310. There are (N+1)×M beam splitters 310. In at least some embodiments, these beam splitters 310 are not polarizing beam splitters. In this array, one column of M beam splitters 310a (the leftmost column in the illustrated embodiment) are initial beam splitters that, as illustrated in FIG. 3B, divide the input beam 312a from the light source 472 (see, FIG. 4) into M beams 312b with each beam then proceeding down a row of the array 300. In at least some embodiments, the beam splitters 310a are arranged to produce the M beams 312b with equal or nearly equal intensity (for example, within 1, 5, or 10% of each other).

The remainder (an N×M array) of the beam splitters 310b divide the M beams 312b into N×M beams 312c (indicated by dots in FIG. 3B). In at least some embodiments, the resulting N×M beams 312c will have equal or nearly equal intensity (for example, within 1, 5, or 10% of each other).

The intensity of the beams 312b, 312c that exit each of the beam splitters 310 can be tailored through the construction of the beam splitter. In at least some embodiments, the use of one or more coatings (for example, adhesive, metallic, or dichroic coatings) on each beam splitter can be used to select the amount of light transmitted through the beam splitter 310 and the amount of light reflected by the interface 311 within the beam splitter 310. Other methods or mechanism (including polarization, as described below) can be used to select the amounts of transmission and reflection of the light by the individual beam splitters 310.

In at least some embodiments, the transmission and reflection of each of these beam splitters 310a, 310b is a function of their location in the array and is selected so that the resulting beams are equal, or approximately equal, in intensity. (Although a uniform beam intensity is often useful, in other embodiments, the beams 312b or the beams 312c may have different intensities and may have non-uniform beam splitting.

For example, some embodiments may benefit from some vapor cells receiving higher intensity light than others to enhance dynamic range or the like.) In embodiments where the intensities are equal or approximately equal, the m-th beam splitter 310a of the first 1×M array has a reflectivity of 1/(M−m+1). Thus, the reflectivity of the first beam splitter 310a is 1/M, the second beam splitter is 1/(M−1), the third beam splitter is 1/(M−2), and so forth. The transmission for the m-th beam splitter 310a is 1-1/(M−m+1). This arrangement leads to beams 312b each having a relatively equal value of reflected light from the array with each beam having ideally 1/M of the input laser power.

Each of the beams 312b go through a similar reflection and transmission process along one of the rows of the array of N×M beam splitters 310b. In each row, the n-th beam splitter 310b (excluding the first beam splitter from this count) of the row has a reflectivity of 1/(N−n+1). The transmission for the n-th beam splitter 310b is 1-1/(N−n+1). This arrangement produces an array of N×M beams 312c with almost equal power, each approximately 1/NM of the original laser power. (For instances in which N=M, the result is $N^2$ beams with each beam having approximately $1/N^2$ of the original laser power.) The orientation of the beam splitters 310b in the N×M array is such that each of these beams 312c will propagate perpendicular to the plane of the array 300, as shown in FIG. 3C.

Figure 4:
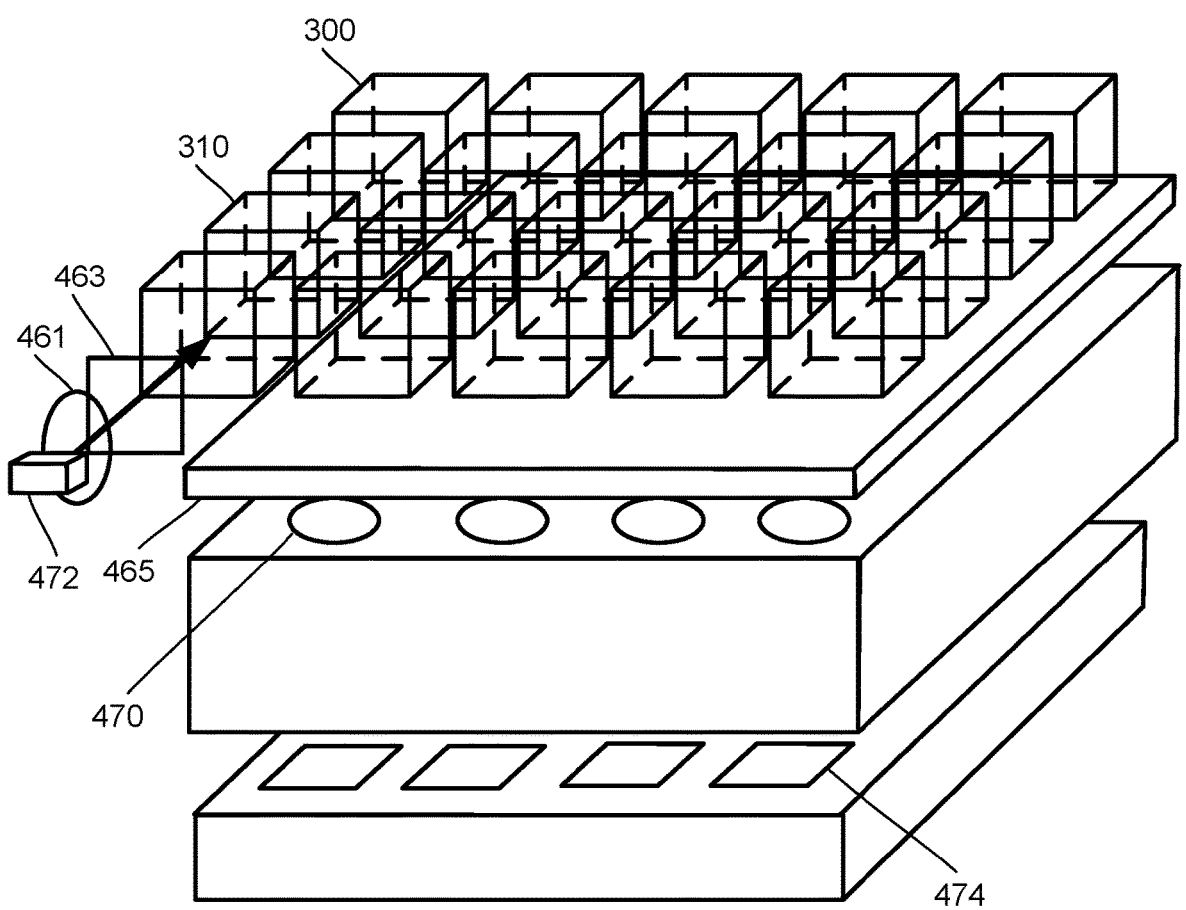
FIG. 4 is a perspective view of one embodiment of an array of magnetometers including the array of beam splitters of FIG. 3A, according to the invention.

FIG. 4 illustrates a portion of magnetic field measurement system with a light source 472 (such as a laser, for example, an edge emitting laser), a lens 461 (for example, a collimating lens), a polarizer 463, the array 300 of beam splitters 310, a quarter waveplate 465, an array of vapor cells 470, and an array of detectors 474. Each of the beams 312c (FIG. 3C) is directed from the array 300 of beam splitters 310 through the quarter waveplate 465 into the array of N×M vapor cells 470 enabling simultaneous operation of all of the OPMs. An N×M array of detectors 474 receives the light that passes through the vapor cells 470. The embodiment of FIG. 4 is just one example of an arrangement, it will be understood that other arrangements can be used.

In at least some embodiments, the light beam 312a of the light source 472 (for example, a surface emitting laser) can be coupled through a fiber (not shown) to the collimating lens 461. This arrangement may be particularly useful if the light source cannot be positioned close to the magnetometer array (for example, due to the production of a magnetic field by the light source).

Figure 5:
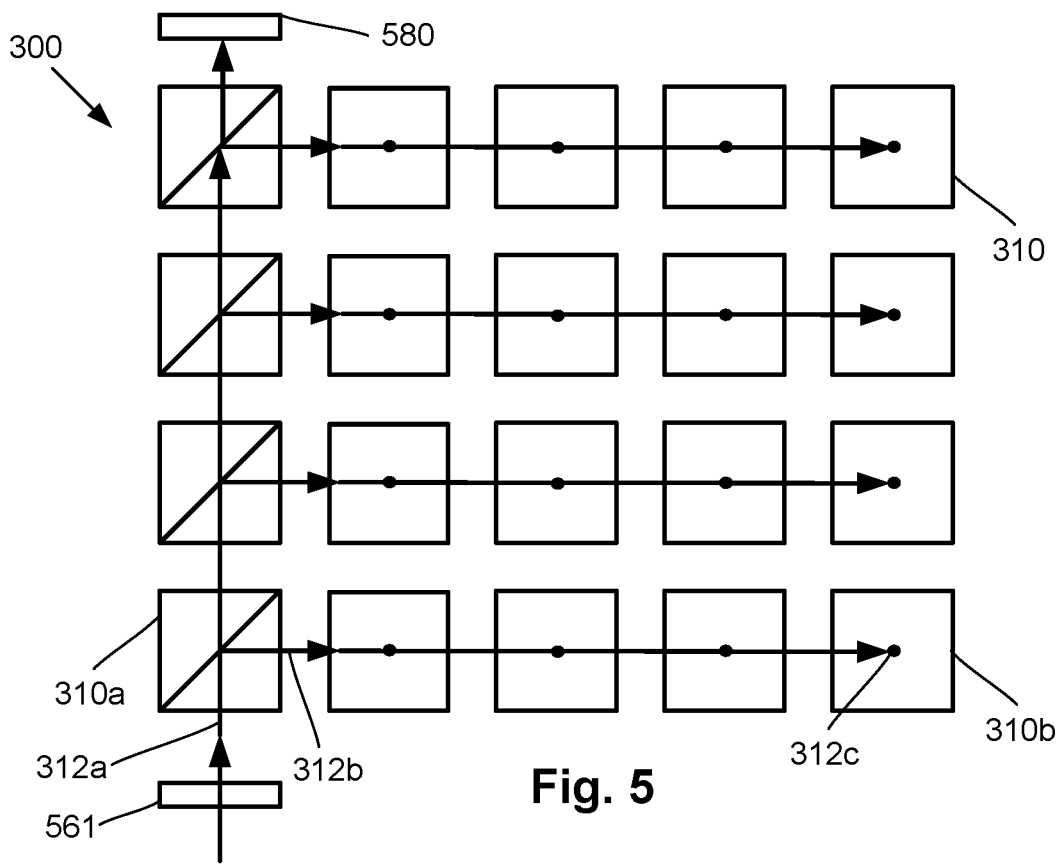
FIG. 5 is a top view of another embodiment of an array of beam splitters for use with an array of magnetometers, according to the invention.

To improve the performance of the magnetometers (e.g., OPMs), a reference detector 580 can be added within the beam path length, as illustrated in FIG. 5. A small portion (for example, no more than 0.5, 1, 2, 5, or 10%) of the initial light beam 312a, which has passed through a polarizer 561, is allowed to pass through all of the initial beam splitters 310a to be detected by the reference detector 580. The light detected by the reference detector 580 can be used, for example, to monitor variations in the light beams 312a, 312b, 312c arising from the light source.

Figure 6:
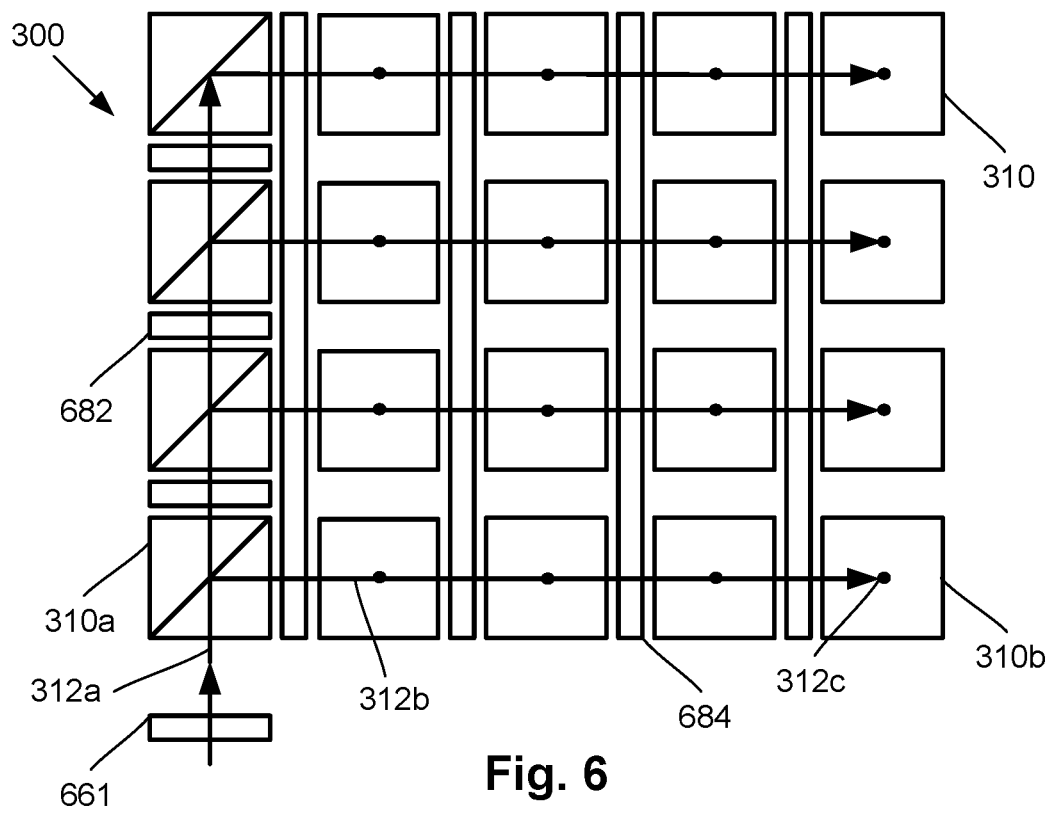
FIG. 6 is a top view of a third embodiment of an array of beam splitters for use with an array of magnetometers, according to the invention.

FIG. 6 illustrates another embodiment of an array 300 of polarizing beam splitters 310 with waveplates 682, 684 positioned between the polarizing beam splitters 310 and an initial polarizer 661. A polarizing beam splitter 310 may transmit one polarization of light and reflect another polarization of light (for example, s- and p-polarizations).

This embodiment utilizes polarization as the basis for splitting the light beam 312a into M light beams 312b and then into N×M light beam 312c. The waveplates 682, 684 are selected to rotate the polarization of the light beam prior to each of the polarizing beam splitters 310 to produce the desired amount of light reflection by the polarizing beam splitter by altering the amount of light in the first and second polarizations. In at least some embodiments, the amount of rotation can be selected using the thickness of the waveplate 682, 684 or the materials of the waveplate or any combination thereof.

In at least some embodiments, the waveplates 682, 684 are selected to result N×M light beams 312c with equal or approximately equal intensity using the formulas provided above for the reflection of light at each beam splitter. The reflection formulas presented above lead directly to the amount of polarization rotation to be accomplished by each of the waveplates 682, 684. In embodiments where the intensities are equal or approximately equal, the waveplate 682 prior to the m-th polarizing beam splitter 310a of the first 1×M array rotates the polarization of the light beam so that the fraction of the light reflected by the m-th polarizing beam splitter is 1/(M−m+1). In each row, the waveplate 684 prior to the n-th polarizing beam splitter 310b (excluding the first polarizing beam splitter from this count) of the row rotates the polarization of the light beam so that the fraction of the light reflected by the n-th polarizing beam splitter is 1/(N−n+1). The transmission for the n-th beam splitter 310b is 1−1/(N−n+1).

In at least some embodiments, the beam splitters 310 of the array 300 cubes may be fused together using an optical adhesive such as, for example, an index-matched optical glue. (In the embodiment of FIG. 6, the beam splitters 310 and waveplates 682, 684 can be fused together using an optical adhesive.) This arrangement may increase the mechanical stability of the array 300 resulting in a single solid unit. The arrangement may also reduce loss and interference effects due to reflection from the surfaces or facets of each beam splitter.

Figure 7A:
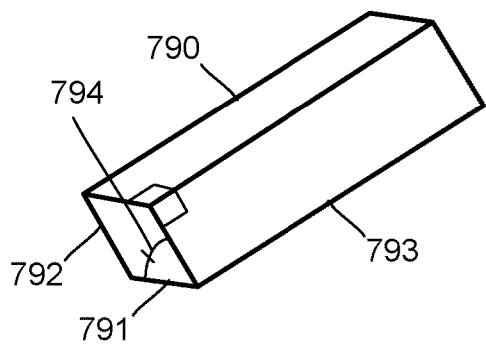
FIG. 7A is a perspective view of a prism for use in an array of beam splitters, according to the invention.
Figure 7B:
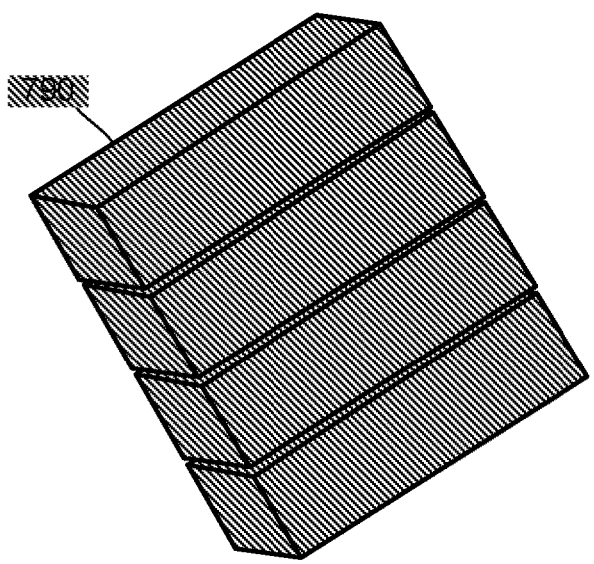
FIG. 7B is a perspective view of several of the prisms coated for use in an array of beam splitters, according to the invention.
Figure 7C:
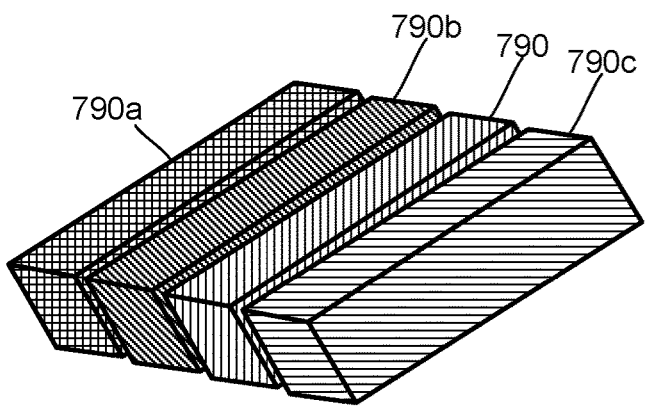
FIG. 7C is a perspective view of an arrangement of different prisms for use in an array of beam splitters, according to the invention.
Figure 7D:
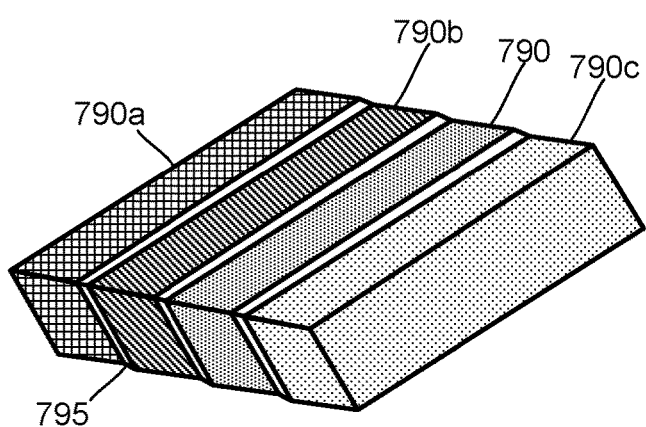
FIG. 7D is a perspective view of an arrangement of different prisms bonded for use in an array of beam splitters, according to the invention.

In at least some embodiments, an array of beam splitters can be constructed using specifically cut material for a smaller number of parts. This arrangement can reduce the number of parts for the N×N output channels, from $N^2$ parts to only N parts. One embodiment is presented in FIGS. 7A to 7D. The first step is to cut glass parts into prisms 790 as illustrated in FIG. 7A. In at least some embodiments, the width 791 of the prism 790 is a, the length 792 of the prism is a×N, the height 793 of the prism is $\sqrt{2}$a, and the angle 794 is 45 degrees. The glass prisms 790 are coated on their largest area surfaces with optical material coatings that will produce the correct reflectivity and transmission for both s-polarization and p-polarization, as illustrated in FIG. 7B. The yield of this step can be improved by stacking the glass prisms as illustrated in FIG. 7B with a number of prisms coated at once. As illustrated in FIG. 7C, different coatings can be used to produce the different prisms 790, 790a, 790b, 790c. The prisms 790, 790a, 790b, 790c are then stacked in the desired order such as, for example, with the prism's reflectivity ordered as described in the reflectivity formulas above. These prisms 790, 790a, 790b, 790c can be bonded permanently using any suitable method, such as optical bonders or adhesive 795, to make a single piece as illustrated in FIG. 7D.

In at least some embodiments, the systems and methods described herein can produce a relatively large number (for example, 12, 16, 25, 36, 64, 100 or more) of output beams from a single light source. In at least some embodiments, multiple light sources can be used with an array of beam splitters associated with each light source. In at least some embodiments, these systems and methods can have a higher tolerance to mechanical vibration, thermal fluctuation, or polarization fluctuation as compared to the conventional systems described above. The systems and methods may also present an arrangement with a more compact volume for a given number of output channels.

In at least some embodiments, when compared to an N×N array of surface emitting lasers, the systems and methods can utilize and arrangement that can produce larger power per output channel for up to about $N^2$ (for example, approximately 100) channels. Moreover, controlling the power stability and wavelength stability of $N^2$ lasers is much more complicated than a single laser, as the array size ($N^2$) grows. Finally, the current to power each of the $N^2$ lasers, and their thermal controller circuits, can produce complex magnetic fields near each of the OPM cells. In contrast, the systems and methods described herein replace these magnetic field producing components with zero field (and low permeability) glass. Therefore, the magnetic field inhomogeneity near the OPM array for the systems described herein may be significantly lower than would be the case for an N×N array of lasers.

In at least some embodiments, the systems and methods described herein can have one or more of the following features: compact design, relatively high mechanical stability, relatively low mechanically induced noise, and relatively high polarization stability.

In at least some embodiments, components of system can be part of a wearable article, such as a helmet, hood, cap, or other shape conformable to a user's head. For example, the vapor cells, array of beam splitters, and detectors can be part of the wearable and portable article. In some embodiments, the light source may also be part of the wearable and portable article.

Examples of magnetic field measurement systems in which the embodiments presented above can be incorporated, and which present features that can be incorporated in the embodiments presented herein, are described in U.S. Patent Application Publications Nos. 2020/0072916; 2020/0056263; 2020/0025844; 2020/0057116; 2019/0391213; 2020/0088811; 2020/0057115; 2020/0109481; 2020/0123416; and 2020/0191883; U.S. patent application Ser. Nos. 16/741,593; 16/752,393; 16/820,131; 16/850,380; 16/850,444; 16/884,672; 16/904,281; 16/922,898; and Ser. No. 16/928,810, and U.S. Provisional Patent Application Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; 62/896,929; 62/898,461; 62/910,248; 62/913,000; 62/926,032;

62/926,043; 62/933,085; 62/960,548; 62/971,132; 62/983,406; 63/031,469; and 63/037,407, all of which are incorporated herein by reference.

Further details discussing different form factors in small, portable, wearable devices and applications thereof are set forth in U.S. patent application Ser. Nos. 16/523,861 and 16/364,338, and U.S. Provisional Patent Application Ser. Nos. 62/829,124; 62/839,405; 62/894,578; 62/859,880; and 62/891,128, all of which are incorporated herein by reference, as well as other references cited above.

The above specification provides a description of the invention and its manufacture and use. Since many embodiments of the invention can be made without departing from the spirit and scope of the invention, the invention also resides in the claims hereinafter appended.

What is claimed as new and desired to be protected by Letters Patent of the United States is:

1. An array of optically pumped magnetometers, comprising:
   an array of vapor cells; and
   an array of beam splitters, wherein the array of beam splitters is arranged into a plurality of columns, including a first column, and a plurality of rows, wherein each row and each column comprises at least two of the beam splitters, wherein the array of beam splitters is configured to receive light into the first column of the array and to distribute that light from the first column into each of the plurality of rows and to distribute the light from each of the rows into a plurality of individual light beams directed toward the vapor cells, wherein the beam splitters are bonded together into a single block using optical adhesive.

2. The array of optically pumped magnetometers of claim 1, wherein the array of vapor cells is an N×M array and the array of beam splitters is an (N+1)×M array, wherein N and M are integers greater than one.

3. The array of optically pumped magnetometers of claim 2, wherein the array of beam splitters is configured to generate N×M beams of light.

4. The array of optically pumped magnetometers of claim 3, wherein the N×M beams of light have intensities that differ by no more than 5% from each other.

5. The array of optically pumped magnetometers of claim 1, wherein the first column has M of the beam splitters and an m-th one of the beam splitters in the first column has a reflectivity of 1/(M−m+1), wherein M is an integer greater than one and m is an integer ranging from 1 to M.

6. The array of optically pumped magnetometers of claim 1, wherein at least one row has a one of the beam splitters from the first column followed by N of the beam splitters after, wherein an n-th one of the N beam splitters has a reflectivity of 1/(N−n+1), wherein N is an integer greater than one and n is an integer ranging from 1 to N.

7. The array of optically pumped magnetometers of claim 1, further comprising a quarter waveplate disposed between the array of beam splitters and the array of vapor cells.

8. The array of optically pumped magnetometers of claim 1, further comprising a light source configured and arranged to direct light into the first column of the array of beam splitters.

9. The array of optically pumped magnetometers of claim 1, further comprising a reference detector configured to receive light that has passed through the beam splitters of the first column.

10. An array of optically pumped magnetometers, comprising:
    an array of vapor cells; and
    an array of polarizing beam splitters, wherein the array of polarizing beam splitters is arranged into a plurality of columns, including a first column, and a plurality of rows, wherein each row and each column comprises at least two of the polarizing beam splitters, wherein the array of polarizing beam splitters is configured to receive light into the first column of the array and to distribute that light from the first column into each of the plurality of rows and to distribute the light from each of the rows into a plurality of individual light beams directed toward the vapor cells.

11. The array of optically pumped magnetometers of claim 10, further comprising waveplates disposed between adjacent ones of the polarizing beam splitters to rotate a polarization of a light beam exiting one of the polarizing beam splitters prior to entering another one of the polarizing beam splitters.

12. A magnetic field measurement system, comprising:
    an array of vapor cells;
    an array of light detectors configured to receive light passing through the vapor cells;
    an array of beam splitters, wherein the array of beam splitters is arranged into a plurality of columns, including a first column, and a plurality of rows, wherein each row and each column comprises at least two of the beam splitters, wherein the array of beam splitters is configured to receive light into the first column of the array and to distribute that light from the first column into each of the plurality of rows and to distribute the light from each of the rows into a plurality of individual light beams directed toward the vapor cells; and
    a wearable article within which the array of vapor cells, array of light detectors and array of beam splitters are disposed.

13. The magnetic field measurement system of claim 12, further comprising at least one magnetic field generator disposed around at least one of the vapor cells to generate a magnetic field in the at least one of the vapor cells.

14. The magnetic field measurement system of claim 12, further comprising a light source configured and arranged to direct light into the first column of the array of beam splitters.

15. The magnetic field measurement system of claim 14, further comprising a computing device coupled to the array of light detectors and the light source.

16. The magnetic field measurement system of claim 12, further comprising a light source disposed in the wearable article and configured and arranged to direct light into the first column of the array of beam splitters.

17. The magnetic field measurement system of claim 12, wherein the first column has M of the beam splitters and an m-th one of the beam splitters in the first column has a reflectivity of 1/(M−m+1), wherein M is an integer greater than one and m is an integer ranging from 1 to M.

18. The magnetic field measurement system of claim 12, wherein at least one row has a one of the beam splitters from the first column followed by N of the beam splitters after, wherein an n-th one of the N beam splitters has a reflectivity of 1/(N−n+1), wherein N is an integer greater than one and n is an integer ranging from 1 to N.

19. The array of optically pumped magnetometers of claim 10, wherein the array of vapor cells is an N×M array and the array of polarizing beam splitters is an (N+1)×M array, wherein N and M are integers greater than one.

20. The array of optically pumped magnetometers of claim 10, further comprising a quarter waveplate disposed between the array of polarizing beam splitters and the array of vapor cells.

* * * * *